US00PP08088P

United States Patent [19]

Heidgen

[11] Patent Number: Plant 8,088

[45] Date of Patent: Jan. 5, 1993

[54] GERANIUM PLANT NAMED 'MIDNIGHT ROSE'

[76] Inventor: Charles F. Heidgen, 821 Walnut St., Batavia, Ill. 60510

[21] Appl. No.: 654,575

[22] Filed: Feb. 13, 1991

[51] Int. Cl.[5] ..... A01H 5/00

[52] U.S. Cl. ..... Plt./87.12

[58] Field of Search ..... Plt./68, 87.12

[56] References Cited

U.S. PATENT DOCUMENTS

P.P. 7,567 6/1991 Schumann ..... Plt. 68

P.P. 7,627 8/1991 Craig ..... Plt. 68

*Primary Examiner*—James R. Feyrer

[57] ABSTRACT

A new and distinct variety of Geranium plant, "Midnight Coral" characterized by its cascading growth habit; its medium-sized, dark green foliage with zoning, its abundant flowers and, its unique, double, bright coral colored flowers and its heat tolerance.

1 Drawing Sheet

BACKGROUND OF THE INVENTION

The present invention, hereinafter referred to by the cultivar name "Midnight Coral" relates to a new and distinct Geranium plant. "Midnight Coral" is a new and improved plant resulting from a planned breeding program as performed by me in my greenhouse at 821 Walnut Street, Batavia, Ill. My breeding program began in Mar. 1977, and has been ongoing since that time. This seedling was initially identified by my records as 80×100P, and was the result of a cross between 78-018F and an unnamed, unreleased seeding which resulted from a selfing of a Friesdorf plant (from a class of unpatented fancy leaf Geraniums) as the seed parent, crossed with "Splash", an unpatented cascade Geranium as the pollen parent.

Being a cross between two market class zonal Geranium plants, it is believed that the botanical classification *Pelargonium×hortorum* would be appropriate for this plant.

Upon recognition of the outstanding characteristics of this plant, it was selected from the progeny of the stated cross, and was set aside for further observation, testing, and was subsequently named "Midnight Coral." Asexual reproduction of "Midnight Coral" has been repeatedly accomplished by the rooting of vegetative cuttings in my greenhouse in Batavia, Ill. Examination of the plants so propagated through a series of propagations has demonstrated that the combination of characteristics herein disclosed for "Midnight Coral" are firmly fixed and retained through succesive generations through asexual reproduction.

SUMMARY OF THE INVENTION

The new and distinguishing characteristics of "Midnight Coral" reside primarily in its cascasing growth habit, its medium-sized, dark green foliage with conspicuous zonation and its abundant blooming habit. This plant also has unique double, medium-sized coral colored semi-double flowers and unusually high heat tolerance. This plant might been seen as a novel and desirable introduction within the industry by a combination of desired traits including:

Being particularly adapted to culture in hanging baskets due to its cascading habit, tendency to prolifically branch, and dense leafy canopy. Forming a dense plant mass completely hiding the top of a basket in about 10 weeks from four plantlets, and a thick plant mass which is wider than it is tall and of mounded form.

Having a generous amount of dark, matt foliage, with exceptionally dark green coloration and very conspicuous zonation over the leaves which are of medium size, but of higher than normal density.

Presenting a large number of well filled umbels of varied states of maturity placed well above the foliage mass, and having a pleasingly coral floret coloration which is attractively, contrastingly high-lighted over and against the dark foliage.

Having a large number of unbels with a geneous number of open, double petal florets of medium size and delicate appearance, borne on pedicels which present florets in a tightly condensed arrangement to form umbels having a fairly tightly compacted and mounded shape.

Presenting a large number of umbels which also vary in stage of maturity which gives the plant an attractive appearance for an extended period of time rather than being one which blooms in discontinuous flushes.

The color definitions to follow have been taken from The Royal Horticultural Colour Chart of The Royal Horticultural Society, London, where presented by the letters R.H.S. followed by a color grouping indication, the number indicating the color patch and the letter indicating the shade, except where color definitions in general terms of ordinary meaning are presented. Plant descriptions were made from specimens grown under greenhouse conditions during daylight hours in Batavia, Ill.

BRIEF DESCRIPTION OF THE DRAWING

The photograph depicts a market unit made up of four market stage specimens of the plant growing in a 10 inch hanging planter, in a stage of inflorescence. The assemblage is shown in side view, depicting the characteristics of branching, leaves, leaf density, leaf coloration and zonation, the number and varied stages of buds and flowers, and the positioning of the flower heads relative to the mass of the plants in the hanging basket.

BOTANICAL DESCRIPTION OF THE PLANT

Botanical classification: *Pelargonium × hortorum.*

Market:

*Class.*—Cascading zonal geranium suitable for planting in hanging baskets.

*Name.*—"Midnight Coral."

Growth: "Midnight Coral" is an exceptionally prolific blooming Geranium. The flowers are double and the flower head or truss is of medium size and quite resistant to shattering. The growth is generally procumbent in attitude which gives it a cascading effect.

*Rate.*—Rapid, producing a typical 10 inch flowering basket in about 10 to 12 weeks from four 2¼ inch platelets using standard commercial culture. This plant has exceptional vigor under normal conditions.

Blooming habit: Exceptionally profuse and continuously blooming plant throughout the year, outdoors during the frost-free period, or in the greenhouse; a mature 10 inch hanging basket commonly producing a range of 20 to 26 flower heads at one time, in varying stages of maturity.

INFLORESCENCE

Flower heads:

*Size.*—2¼ to 3⅞ inches across when the florets are fully open.

*Count.*—20 to 26 presented at one time.

Truss:

*Size.*—Medium size ranges from about 2 to 2¾ inches in diameter.

*Shape.*—Rather tight, forming ½ of a flattened globe as it opens.

*Number of florets.*—Variable, range of from about 35 to 50, average 39 to 42.

*Lasting quality.*—Average. Blooms remain 5 to 10 days and may last longer in cool, dry weather.

*Sepals.*—Shape — Pointed and of medium width. Color — Same as leaves.

*Color.*—Red Group R.H.S. 4 2 D.

*Form.*—Long, somewhat pointed and fat.

Florets:

*Number.*—8 to 16.

*Form.*—Flat to cupped.

*Size.*—Ranging from 1¼ inch to 1⅝ inches across an open floret.

Petals:

*Number.*—About 10 to 14.

*Size.*—Ranging from about 11/16 to 13/16 inches long to about 5/16 to 7/16 inches wide.

*Texture.*—Soft.

*Appearance.*—Bright.

Petaloids:

*Number.*—About 4 to 7.

*Shape.*—Variable, often misshapen.

*Color.*—Similar to that of the petals.

*Size.*—About ½ to ⅝ inches long and ¼ to ⅜ inches wide

Sepals:

*Number.*—Usually 5.

*Color.*—Abou like that of the leaves.

Pedicel:

*Length.*—About ⅞ to 1 inch.

*Color.*—RHS Greyed Purple, 185 A.

Peduncle:

*Arises.*—Fron node, opposed to leaf petiole.

*Pubescence.*—Normal.

*Color.*—R.H.S. Greyed Purple 183A.

REPRODUCTIVE ORGANS

Androecium:

*Stamens.*—Number — 4 to 5. Shape — Ribbon-like filaments jointed at bases. Color — Rose purple. Anther attachment — Versatile.

*Anthers.*—Number — 3 to 5. Shape — Normal, well developed. Color — Purple.

Gynoecium:

*Pistil.*—Number — One, compound. Length — About within the range of 3/32 to 5/32 inches.

*Stigma.*—Color — Purple.

*Style.*—Color — Green.

*Ovary.*—Size — Within about 1/32 to 1/16 inches long.

Fertility: Normal, viable seed is produced sparsely.

Behaviour: Once the plant begins to bloom, it has an exceptionally prolific blooming habit and yields a striking display of medium-sized, double bright coral flowers against its medium-sized dark green foliage with zoning.

General observations: Inflorescence is of medium size, and of somewhat tight heads which are in attractive contrast to the dark foliage of the plant and generally rounded in shape and measure up to about 3⅞ inches across. High floret, petal and petaloid counts make umbels appear as dense balls at optimum stage of opening. Flowers have very high tolerance to heat when compared to those of other varieties.

STEM

Thickness: Medium slim.

Internodes: Short.

Branching: Free breaking.

Attitude: Procumbent habit.

FOLIAGE

Leaves:

*Quantity.*—Abundent.

*Shape.*—Reniform.

*Size.*—Largest leaves range from about 1⅝ to about 2½ inches wide.

*Margin.*—Crenate.

*Texture.*—Matt, lightly pubescent.

*Coloration.*—Leaves a much darker appearing green tone than normally seen in Geraniums per se, R.H.S. Green Group 147A, with wide zones of brown hue R.H.S. Brown Group 200A. Zonation is centrally located on the leaf surfaces, and concentric to the point of petiole attachment and with green surface portions both inside and outside the zonal band.

Petioles:

*Texture.*—Lightly pubescent.

*Length.*—About 1⅜ to 1⅝ inches.

*Color.*—Yellow Green Group R.H.S. 147A.

"Midnight Coral" is comparable to "Flame Delight" with which it shares market class, but is easily distinguishable therefrom in terms of flower color; "Midnight Coral" having bright coral petal coloration, while the petals of "Flame Delight" are more scarlet; and by vigor, "Midnight Coral" being much more vigorous. "Midnight Coral" is readily distinguished from "Midnight Rose" by having florets which are much more double, and of different coloration and by having a leaf attitude which more closely follows the shape of the plant mass and by having leaf zonation which is darker and more conspicuous.

I claim:

1. A new and distinct variety of Geranium plant, substantially as shown and described, characterized by its cascading growth habit; its unique, double, bright coral colored flowers and its heat tolerance.

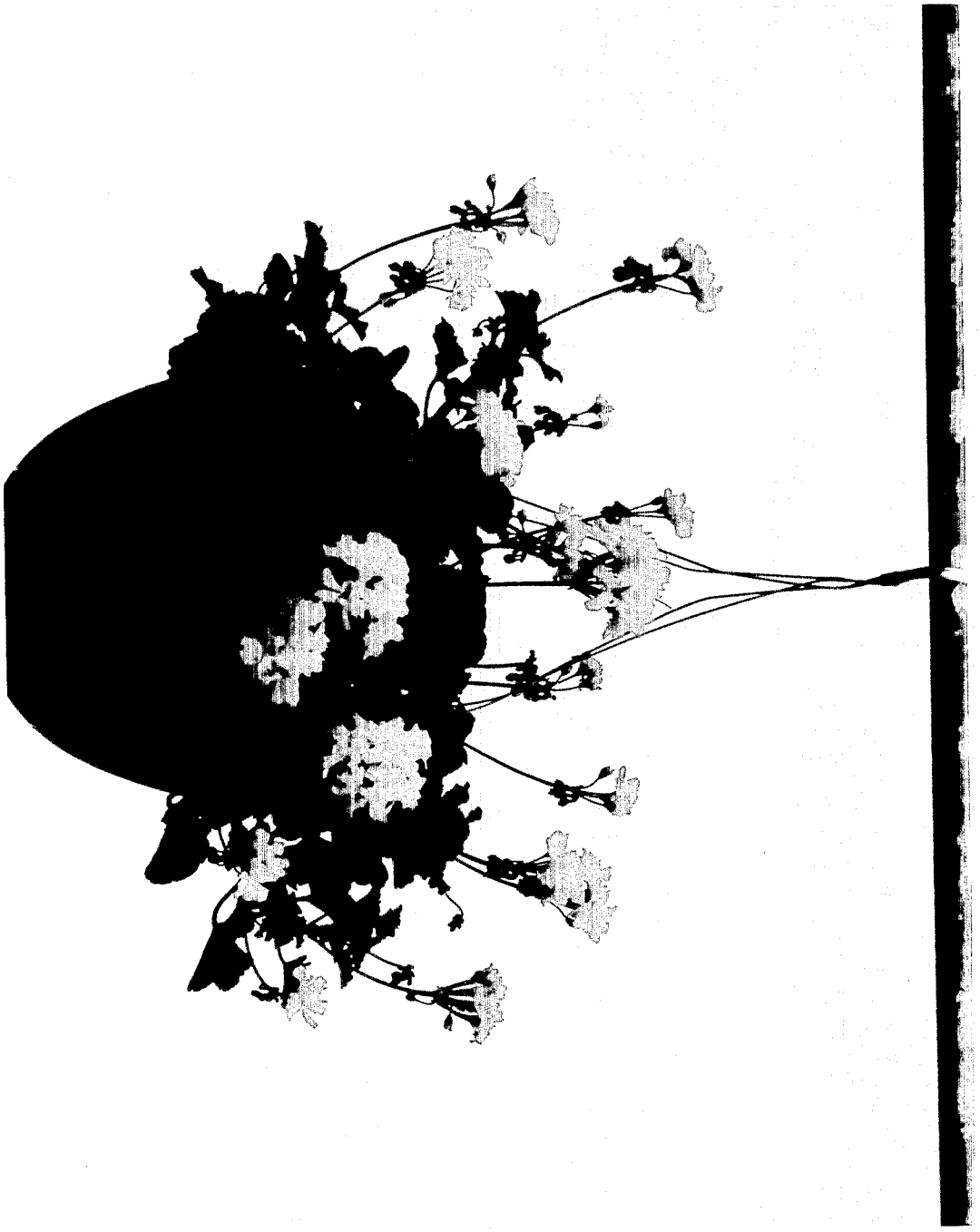

* * * * *